United States Patent
Kitagawa et al.

(10) Patent No.: US 6,175,025 B1
(45) Date of Patent: Jan. 16, 2001

(54) PROCESS FOR SYNTHESIZING METALLOCENE COMPOUNDS

(75) Inventors: Yuichi Kitagawa, Kawasaki; Koji Otaka, Tokushima; Tomoya Kubo, Tokushima; Eiji Takeichi, Tokushima, all of (JP)

(73) Assignee: Asahi Kasei Kogyo Kabushiki Kaisha (JP)

( * ) Notice: Under 35 U.S.C. 154(b), the term of this patent shall be extended for 0 days.

(21) Appl. No.: 09/486,273

(22) PCT Filed: Jun. 24, 1998

(86) PCT No.: PCT/JP98/02819
§ 371 Date: Feb. 23, 2000
§ 102(e) Date: Feb. 23, 2000

(87) PCT Pub. No.: WO99/67260
PCT Pub. Date: Dec. 29, 1999

(30) Foreign Application Priority Data

Dec. 25, 1996 (JP) .................................................. 8-345421
Dec. 23, 1997 (JP) .................................................. 9-354685

(51) Int. Cl.$^7$ ................................ C07F 17/00; C07F 7/00

(52) U.S. Cl. ............................... 556/22; 556/53; 502/107; 502/117; 526/160; 526/943

(58) Field of Search ..................... 556/22, 53; 502/103, 502/117; 526/160, 943

(56) References Cited

U.S. PATENT DOCUMENTS 6,063,949 * 5/2000 Aulbach et al. ........................ 556/53

FOREIGN PATENT DOCUMENTS

0749985 A2 * 12/1996 (EP).
9-3085 1/1997 (JP).

* cited by examiner

Primary Examiner—Porfirio Nazario-Gonzalez
(74) Attorney, Agent, or Firm—Pennie & Edmonds LLP

(57) ABSTRACT

A di-substituted metallocene compound having good quality can be synthesized completely at a low cost in a high yield in a easy manner by reacting a metallocene dihalide with a Grignard reagent which is a compound represented by formula (I): RMgX (wherein R represents an aryl, benzyl or diaryl phosphinomethylene group which may have a substituent and X represents a halogen element) under specified conditions.

7 Claims, No Drawings

PROCESS FOR SYNTHESIZING METALLOCENE COMPOUNDS

TECHNICAL FIELD

The present invention relates to a process for synthesizing metallocene compounds which can be effectively used as a catalyst for organic synthesis, a polymerization catalyst, a catalyst for hydrogenation of a low-molecular weight compound or high-molecular weight compound, etc.

BACKGROUND ART

Metallocene compounds are useful as catalysts and various metallocene compounds have been known.

Several synthesizing processes are known as processes for preparing a useful metallocene compound. However, in substituting the halogens of metallocene dihalide with a substituent, if the substituent has a high molecular weight, makes the substituted product bulky, or is an aromatic compound, etc., there have been problems that an exchange reaction of the halogen does not proceed sufficiently, resulting in a reduced yield and that a large amount of by-products are produced which makes post-treatment difficult.

For example, a conventionally known process for synthesizing an aryl metallocene compound is to react a metallocene dihalide with an aryl alkali metal compound at room temperature or at the reflux temperature of a solvent employed for the reaction (as described in L. Summers et al., J. Am. Chem. Soc., 77, p.3604, (1955), M. D. Rausch et al., J. Organometall. Chem., 10, p.127 (1967), etc.). However, since the above-described process is accompanied with the side reaction such as reduction of the metal atom of a metallocene, a target product cannot be obtained in a high yield. In order to obtain a high-purity aryl metallocene compound, an additional step for purification such as recrystallization is necessary, which is not economical.

On the other hand, known is a process for synthesizing a diaryl metallocene compound by reacting a metallocene dihalide (e.g., metallocene dichloride) with an aryl alkali metal (e.g., an aryl lithium) in a polar solvent at 0° C. or lower (as described in JP-B-2-34360, JP-B-63-60027 and JP-B-63-60028: the term "JP-B" as used herein means an "examined published Japanese patent publication"). This process requires the use of an expensive and highly dangerous chemical such as an alkali metal or diethyl ether. The alkali metal is very dangerous in handling because it ignites by the water content in the air. In addition, the alkali metal must be used in an amount not less than 2 times the theoretical amount, which necessarily leads to a cost increase. Since the target aryl metallocene compound is an industrially useful catalyst for preparation or hydrogenation of a high-molecular weight compound having a high stereoregularity, there is a strong demand for the development of its preparation process which is safe and inexpensive, which facilitates post-treatment and which permits preparation in a high yield.

In addition, known is a process for preparing a mono-substituted metallocene compound by reacting a metallocene dihalide with an alkyl Grignard reagent (as described, for example, in W. P. Long et al., J. Am. Chem. Soc., 82, p.1953 (1960), H. C. Beachell et al., Inorg. Chem., 4, p.1133 (1965), etc.). A preparation process of a di-substituted metallocene compound is however not described in the above documents.

A process for synthesizing a di-substituted dimethyl metallocene compound by reacting a metallocene dihalide with a methyl Grignard reagent at 25° C. in a solvent of THF is also known (as described in T. S. Piper et al., J. Inorg. Nucl. Chem., 3, p.104 (1956), etc.). The yield brought by this process is, however, 1% and is markedly low. It is reported in WO97/09336 that a di-substituted dimethyl metallocene compound can be obtained in a good yield by reacting a metallocene dihalide with a methyl Grignard reagent at −5° C. for 10 minutes or −5° C. for 1 hour.

A process for preparing a di-substituted metallocene compound having a substituent other than a methyl group by using a Grignard reagent has not yet known and a process for preparing such a di-substituted metallocene compound at a high purity in a high yield sufficient for industrial production is desired.

An object of the present invention is therefore to solve the above-described problems upon synthesis of a metallocene compound and to provide a process for safely and easily synthesizing, at a low cost and in a high yield, a di-substituted metallocene compound substituted with an aryl, benzyl or diaryl phosphinomethylene group.

DISCLOSURE OF THE INVENTION

As a result of various investigations, the present inventors have surprisingly found that the above-described di-substituted metallocene compound can be synthesized in a high yield by reacting a metallocene dihalide with a Grignard reagent under specified reaction conditions. Thus, the present invention was completed.

That is, the present invention relates to the following processes.

(1) A process for synthesizing a di-substituted metallocene compound, which comprises reacting a metallocene dihalide with a compound represented by formula (I): RMgX (wherein R represents an aryl, benzyl or diaryl phosphinomethylene group which may have a substituent, and X represents a halogen element) to produce a di-substituted metallocene compound.

(2) The process for synthesizing a metallocene compound according to the above (1), wherein the reaction is effected under conditions which do not cause a side reaction.

(3) The process for synthesizing a metallocene compound according to the above (1), wherein the compound of formula (I) is added dropwise to a solution containing the metallocene dihalide at a temperature lower than 25° C. but not lower than −30° C. over 3 to 20 hours.

(4) The process for synthesizing a metallocene compound according to the above (3), wherein the compound of formula (I) is added dropwise at a temperature ranging from 15° C. to −25° C. over 5 to 15 hours.

(5) The process for synthesizing a metallocene compound according to any one of the above (1) to (4), wherein the compound of formula (1) in a molar amount of 0.9 to 1.5 times the theoretical amount with respect to the metallocene dihalide is reacted with the solution containing the metallocene dihalide.

(6) The process for synthesizing a metallocene compound according to any one of the above (1) to (4), wherein the solvent of the solution containing the metallocene dihalide is at least one of a linear ether and a cyclic hydrocarbon.

(7) The process for synthesizing a metallocene compound according to the above (1) to (4), wherein the metal atom of the metallocene dihalide is Ti, Zr or Hf.

In the present invention, a metallocene dihalide is reacted with a Grignard reagent under specified conditions, which makes it possible to substitute the halogens of the metallocene dihalide with substituents such an aryl, benzyl or diaryl phosphinomethylene group without using an alkali metal compound which is a cause for the drawback of the conventional process and to prepare a highly-pure di-substituted metallocene compound in a high yield without an economical burden due to a large amount of a loss caused by cumbersome operations such as recrystallization or by purification.

Moreover, in the present invention, better results can be obtained by specifying the reaction solvent.

Furthermore, it is preferred that the metal of the metallocene halide is a specific metal as defined above, because the resulting di-substituted metallocene compound has higher usefulness

BEST MODES FOR CARRYING OUT THE INVENTION

In the present invention, the metallocene compound can be obtained by reacting a metallocene dihalide with a compound represented by formula (I) (hereinafter sometime referred to as "Grignard reagent") under the conditions not causing a side reaction. The term "metallocene dihalide" as used herein means a compound in which two molecules of a cyclopentadiene ring or of a substituted cyclopentadiene ring and two halogen atoms are coordinated per center metal. The term "di-substituted metallocene compound" as used herein means a metallocene compound in which each of the two halogen atoms of a metallocene dihalide have been substituted with R of formula (I). In the present invention, in order to preventing occurrence of a side reaction, synthesis is preferably carried out by adding a metallocene dihalide to an organic solvent, stirring the mixture and then adding dropwise a Grignard reagent of formula (I) to the resulting solution.

Taking into account the yield and purity of the target compound, the temperature upon dropwise addition of the Grignard reagent of formula (I) to the metallocene dihalide-containing organic solvent is lower than 25° C. but not lower than −30° C., preferably 15 to −25° C., more preferably −5 to −20° C. Dropwise addition is preferably carried out over a period of from 3 to 20 hours, preferably from 5 to 15 hours, more preferably around 10 hours.

When the temperature upon dropwise addition is lower than −30° C., the reaction requires too much time, which tends to cause deterioration of the product. Temperatures not lower than 25° C., on the other hand, easily reduce the transition metal of the metallocene dihalide and form a by-product, leading to a tendency to decrease the yield.

The target products which can be obtained by the synthesizing process of the present invention may include compounds readily affected by a high or low temperature. Therefore, the temperature upon dropwise addition preferably falls within the above-described range in order to suppress the decomposition of the target product as much as possible and complete the reaction.

When the dropwise addition is carried out for less than 3 hours, the reaction is not sufficiently completed and impurities are inevitably mixed in the reaction product, leading to a tendency to cause a problem such as deterioration in the quality of the product. This is presumed to occur because existence of a large amount of the Grignard reagent relative to the metallocene dihalide causes simultaneous progress of a substitution reaction of the halogen and a reduction reaction of the transition metal. In addition, when the dropwise addition time is too short, the substitution reaction does not proceed sufficiently, leading to a tendency to the formation of only a mono-substituted product or the formation of a mixture of mono-substituted and di-substituted products. When the dropwise addition time exceeds 20 hours, on the other hand, the halogen atoms of the metallocene dihalide are presumed to be properly substituted with the R groups of formula (I), but too long dropwise addition time tends to cause a problem such as the product which has already been synthesized is deteriorated with time.

In the present invention, it is preferred to add the Grignard reagent of formula (I) in a molar amount of 0.9 to 1.5 times, preferably 0.95 to 1.20 times, more preferably 1.10 to 1.15 times the theoretical amount relative to the metallocene dihalide. The theoretical molar ratio of the Grignard reagent and the metallocene dihalide for use in the present invention is 2:1 (this theoretical ratio corresponds to the case where all the halogen atoms of the metallocene dihalide are each substituted with R of formula (I)).

In the present invention, molar amounts of the Grignard reagent of formula (I) less than 0.9 time tend to cause a side reaction due to the existence of an unstable reaction intermediate, thereby causing a deterioration in the quality and yield of the target compound. Molar amounts of the Grignard reagent of formula (I) exceeding 1.5 times, on the other hand, require an additional step for decomposing the remaining Grignard reagent, which makes the preparation process complex and, due to the existence of a large amount of Mg remaining in the crystals, tends to deteriorate the quality of the target compound.

In the present invention, as the Grignard reagent which is the compound of formula (I), a commercially available Grignard reagent can be employed. It may also be prepared by an ordinarily known synthesizing process.

In formula (I), R represents an aryl, benzyl or diaryl phosphinomethylene group which may have one or more substituents, which substituents may be the same or different.

When the aryl, benzyl (benzene ring of the benzyl group) or diaryl phosphinomethylene group represented by R of formula (I) has a substituent, examples of the substituent include linear or branched alkyl or alkoxy groups each having 1 to 20 carbon atoms, aryloxy groups, alkylsilyl groups, arylsilyl groups, alkoxysilyl groups and aryloxysilyl groups. Any of the substituents can be employed as long as it does not disturb the present invention.

Examples of the aryl group represented by R of formula (I) include $C_{6-14}$ aryl groups which may have one or more substituents, which substituents may be the same or different. Specific examples of the aryl group include phenyl, tolyl, ethylphenyl, butylphenyl, dimethylphenyl, trimethylphenyl, methoxyphenyl, dimethoxyphenyl, ethoxyphenyl, ethylmethoxyphenyl, phenoxyphenyl, trimethylsilylphenyl, triethylsilylphenyl, phenyldimethylsilylphenyl, diphenylmethylsilylphenyl, triphenylsilylphenyl, trimethoxysilylphenyl, triphenoxysilylphenyl, phenoxydimethylphenyl, naphthyl and anthryl.

Examples of the benzyl group represented by R of formula (I) include benzyl groups which may have, on the benzene ring, one or more substituents, which substituents may be the same or different. Specific examples include benzyl, methylbenzyl, methoxybenzyl, phenylbenzyl, phenoxybenzyl and trimethylsilylbenzyl.

Examples of the diaryl phosphinomethylene group represented by R of formula (I) include those represented by the formula: $CH_2PR'R''$ (R' and R'' each represents a $C_{6-14}$ aryl group which may have one or more substituents, which substituents may be the same or different). Specific examples include diphenyl phosphinomethylene, ditolyl phosphinomethylene, tolylphenyl phosphinomethylene, bis-methoxyphenyl phosphinomethylene and bisphenoxyphenyl phosphinomethylene.

In the present invention, as the metallocene dihalide, a commercially available metallocene dihalide can be employed. It can also be synthesized by the ordinarily known process.

Examples of the metal of the metallocene dihalide for use in the present invention include the transition metals belonging to Groups 4, 5 and 6 of the periodic table. Specific examples thereof include titanium, vanadium, chromium, iron, cobalt, nickel, zirconium, ruthenium and hafnium. Of these, the titanium (Ti), zirconium (Zr) and hafnium (Hf) are preferred. Examples of the halogen of the metallocene dihalide include bromine, chorine and iodine, of which the chlorine and bromine are preferred.

The cyclopentadienyl ring of the metallocene dihalide for use in the present invention may have a substituent or may be crosslinked. If it has a substituent, examples of the substituent include $C_{1-12}$ hydrocarbon groups and $C_{1-12}$ alkylsilyl groups. Any of the substituents can be employed as long as it does not disturb the present invention. The cyclopentadienyl ring may be substituted with such a substituent at each of the mono-, di-, tri-, tetra- and penta-positions. Examples of the $C_{1-12}$ hydrocarbon group include linear hydrocarbon groups, hydrocarbon groups having a side chain, aliphatic hydrocarbon groups and aromatic hydrocarbon groups. Examples of the $C_{1-12}$ alkylsilyl group include those represented by RR'R"Si— and —SiRR'— (wherein R, R' and R" each represents a $C_{1-12}$ alkyl group), respectively and form a ring on the same cyclopentadienyl ring or form a crosslinked structure between different cyclopentadienyl rings. Examples include fluorenyl, indenyl, tetrahydroindenyl, methylene, ethylene, —C(CH$_3$)$_2$—, C(C$_2$H$_5$)$_2$—, —Si(CH$_3$)$_2$— and —Si(C$_2$H$_5$)$_2$—.

Specific examples of the metallocene dihalide for use in the present invention include
bis(cyclopentadienyl)titanium dichloride,
bis(cyclopentadienyl)titanium dibromide,
bis(methylcyclopentadienyl)titanium dichloride,
bis(methylcyclopentadienyl)titanium dibromide,
bis(dimethylcyclopentadienyl)titanium dichloride,
bis(dimethylcyclopentadienyl)titanium dibromide,
bis(trimethylcyclopentadienyl)titanium dichloride,
bis(trimethylcyclopentadienyl)titanium dibromide,
bis(tetramethylcyclopentadienyl)titanium dichloride,
bis(tetramethylcyclopentadienyl)titanium dibromide,
bis(pentamethylcyclopentadienyl)titanium dichloride,
bis(pentamethylcyclopentadienyl)titanium dibromide,
bis(diisopropylcyclopentadienyl)titanium dichloride,
bis(diisopropylcyclopentadienyl)titanium dibromide,
bis (methylethylcyclopentadienyl) titanium dichloride,
bis(methylethylcyclopentadienyl)titanium dibromide,
bis(methylpropylcyclopentadienyl)titanium dichloride,
bis(methylpropylcyclopentadienyl)titanium dibromide,
bis(methylbutylcyclopentadienyl)titanium dichloride,
bis(methylbutylcyclopentadienyl)titanium dibromide,
ethylenebis(cyclopentadienyl)titanium dichloride,
ethylenebis(cyclopentadienyl)titanium dibromide,
dimethylsilylenebis(cyclopentadienyl)titanium dichloride,
dimethylsilylenebis(cyclopentadienyl)titanium dibromide,
dimethylsilylenebis(methylcyclopentadienyl)titanium dichloride,
dimethylsilylenebis(methylcyclopentadienyl)titanium dibromide,
dimethylsilylenebis(isopropylcyclopentadienyl)titanium dichloride,
dimethylsilylenebis(isopropylcyclopentadienyl)titanium dibromide,
dimethylsilylenebis(dimethylcyclopentadienyl)titanium dichloride,
dimethylsilylenebis(dimethylcyclopentadienyl)titanium dibromide,
dimethylsilylenebis(methylethylcyclopentadienyl)titanium dichloride,
dimethylsilylenebis(methylethylcyclopentadienyl)titanium dibromide,
bis(cyclopentadienyl)zirconium dichloride,
bis(cyclopentadienyl)zirconium dibromide,
bis(methylcyclopentadienyl)zirconium dichloride,
bis(methylcyclopentadienyl)zirconium dibromide,
bis(dimethylcyclopentadienyl)zirconium dichloride,
bis(dimethylcyclopentadienyl)zirconium dibromide,
bis(trimethylcyclopentadienyl)zirconium dichloride,
bis(trimethylcyclopentadienyl)zirconium dibromide,
bis(tetramethylcyclopentadienyl)zirconium dichloride,
bis(tetramethylcyclopentadienyl)zirconium dibromide,
bis(pentamethylcyclopentadienyl)zirconium dichloride,
bis(pentamethylcyclopentadienyl)zirconium dibromide,
bis(diisopropylcyclopentadienyl)zirconium dichloride,
bis(diisopropylcyclopentadienyl)zirconium dibromide,
bis(methylethylcyclopentadienyl)zirconium dichloride,
bis(methylethylcyclopentadienyl)zirconium dibromide,
bis(methylpropylcyclopentadienyl)zirconium dichloride,
bis(methylpropylcyclopentadienyl)zirconium dibromide,
bis(methylbutylcyclopentadienyl)zirconium dichloride,
bis(methylbutylcyclopentadienyl)zirconium dibromide,
ethylenebis(cyclopentadienyl)zirconium dichloride,
ethylenebis(cyclopentadienyl)zirconium dibromide,
dimethylsilylenebis(cyclopentadienyl)zirconium dichloride,
dimethylsilylenebis(cyclopentadienyl)zirconium dibromide,
dimethylsilylenebis(methylcyclopentadienyl)zirconium dichloride,
dimethylsilylenebis(methylcyclopentadienyl)zirconium dibromide,
dimethylsilylenebis(isopropylcyclopentadienyl)zirconium dichloride,
dimethylsilylenebis(isopropylcyclopentadienyl)zirconium dibromide,
dimethylsilylenebis(dimethylcyclopentadienyl)zirconium dichloride,
dimethylsilylenebis(dimethylcyclopentadienyl)zirconium dibromide,
dimethylsilylenebis(methylethylcyclopentadienyl) zirconium dichloride,
dimethylsilylenebis(methylethylcyclopentadienyl) zirconium dibromide,
bis(cyclopentadienyl)hafnium dichloride,
bis(cyclopentadienyl)hafnium dibromide,
bis(methylcyclopentadienyl)hafnium dichloride,
bis(methylcyclopentadienyl)hafnium dibromide,
bis(dimethylcyclopentadienyl)hafnium dichloride,
bis(dimethylcyclopentadienyl)hafnium dibromide,
bis(trimethylcyclopentadienyl)hafnium dichloride,
bis(trimethylcyclopentadienyl)hafnium dibromide,
bis(tetramethylcyclopentadienyl)hafnium dichloride,
bis(tetramethylcyclopentadienyl)hafnium dibromide,
bis(pentamethylcyclopentadienyl)hafnium dichloride,
bis(pentamethylcyclopentadienyl)hafnium dibromide,
bis(diisopropylcyclopentadienyl)hafnium dichloride,
bis(diisopropylcyclopentadienyl)hafnium dibromide,
bis(methylethylcyclopentadienyl)hafnium dichloride, bis(methylethylcyclopentadienyl)hafnium dibromide,
bis(methylpropylcyclopentadienyl)hafnium dichloride,
bis(methylpropylcyclopentadienyl)hafnium dibromide,
bis(methylbutylcyclopentadienyl)hafnium dichloride,
bis(methylbutylcyclopentadienyl)hafnium dibromide,
ethylenebis(cyclopentadienyl) hafnium dichloride,
ethylenebis(cyclopentadienyl)hafnium dibromide,
dimethylsilylenebis(cyclopentadienyl)hafnium dichloride,
dimethylsilylenebis(cyclopentadienyl)hafnium dibromide,
dimethylsilylenebis(methylcyclopentadienyl)hafnium dichloride,
dimethylsilylenebis(methylcyclopentadienyl)hafnium dibromide,
dimethylsilylenebis(isopropylcyclopentadienyl)hafnium dichloride,
dimethylsilylenebis(isopropylcyclopentadienyl)hafnium dibromide,
dimethylsilylenebis(dimethylcyclopentadienyl)hafnium dichloride,
dimethylsilylenebis(dimethylcyclopentadienyl)hafnium dibromide,
dimethylsilylenebis(methylethylcyclopentadienyl)hafnium dichloride and
dimethylsilylenebis(methylethylcyclopentadienyl)hafnium dibromide.

As the solvent for the metallocene dihalide, anhydrous organic solvents can be used in the present invention. Preferred examples thereof include linear ethers and cyclic hydrocarbons and mixtures thereof. Specific examples of the linear ether include diethyl ether and 1,2-dimethoxyethane. Specific examples of the cyclic hydrocarbon include cyclohexane, benzene, toluene, xylene and the above-exemplified aromatic hydrocarbons substituted by at least one halogen atom. Among them, xylene, toluene and 1,2-dimethoxyethane are preferred as the solvent for the synthesis.

In substituting the two halogen atoms of the metallocene dihalide using a Grignard reagent, if a cyclic ether (e.g., tetrahydrofuran and 1,4-dioxane) or a chlorine-series hydrocarbon (e.g., dichloromethane and chloroform) is used as a synthesizing solvent, it tends to result in insufficient progress of the substitution reaction with the Grignard reagent, to thereby readily leave a large amount of magnesium or halogen in the target compound or form a by-product, leading to a deterioration in the quality of the target product.

EXAMPLES

Examples of the present invention will be described below, but the invention is not limited thereto.

Example 1

In a reactor having an internal volume of 200 liters, 110 liters of xylene as a solvent and 8817 g (35.41 moles) of titanocene dichloride were charged, followed by sufficient stirring. The internal temperature was then cooled to –10° C. To the resulting suspension, 45 liters (1.810 moles/liter, 81.45 moles, 1.15 molar times the theoretical amount relative to the titanocene dichloride) of a tetrahydrofuran (THF) solution of p-tolylmagnesium chloride which had been synthesized by the Grignard reaction was added dropwise at the internal temperature of –8 to –10° C. over 10 hours.

After completion of the dropwise addition, stirring was continued for 1 hour at the same temperature. The temperature was then gradually raised to room temperature and, at room temperature, stirring was continued for further 3 hours to complete the reaction. The precipitate thus formed was filtered off and the filtrate was concentrated until crystallization occurred. When the crystals appeared, the concentration was terminated and the filtrate was cooled until it became 0° C., so as to sufficiently effect crystallization.

The resulting crystals were thereafter collected by separation, followed by vacuum drying, to thereby obtain 8549 g (yield: 67.0%) of di-p-tolylbis($\eta$-cyclopentadienyl)titanium as orange crystals. The resulting product was found to have a Ti content of 13.26% (theoretical value: 13.29%), remaining Mg content of 1 ppm and remaining Cl content of 10 ppm. Thus, the quality of the product was fully satisfactory.

Example 2

In a reactor having an internal volume of 200 liters, 110 liters of 1,2-dimethoxyethane as a solvent and 8811 g (30.14 moles) of zirconocene dichloride were charged, followed by sufficient stirring. The internal temperature was then cooled to –20° C. To the resulting suspension, 41.34 liters (1.750 moles/liter, 72.34 moles, 1.20 molar times the theoretical amount relative to the zirconocene dichloride) of a THF solution of phenylmagnesium chloride which had been synthesized by the Grignard reaction was added dropwise at the internal temperature of –15 to –20° C. over 10 hours.

After completion of the dropwise addition, stirring was continued for 1 hour at the same temperature. The temperature was then gradually raised to room temperature and, at room temperature, stirring was continued for further 3 hours to complete reaction. The precipitate thus formed was filtered off and the filtrate was concentrated until crystallization occurred. When the crystals appeared, the concentration was terminated and the filtrate was cooled until it became 0° C., so as to sufficiently effect crystallization.

The resulting crystals were the collected by separation, followed by vacuum drying, to thereby obtain 6295 g (yield: 65.3%) of diphenyl-bis($\eta$-cyclopentadienyl)zirconium as white crystals. The resulting product was found to have a Zr content of 28.46% (theoretical value: 28.52%), remaining Mg content of 1 ppm and remaining Cl content of 15 ppm. Thus, the quality of the product was fully satisfactory.

Example 3

In a reactor having an internal volume of 200 liters, 110 liters of 1,2-dimethoxyethane as a solvent and 8817 g (35.41 moles) of titanocene dichloride were charged, followed by sufficient stirring. The internal temperature was then cooled to –20° C. To the resulting suspension, 49 liters (1.650 moles/liter, 81.45 moles, 1.15 molar times the theoretical amount relative to titanocene dichloride) of a THF solution of benzylmagnesium chloride which had been synthesized by the Grignard reaction was added dropwise at the internal temperature of –15 to –20° C. over 9 hours.

After completion of the dropwise addition, stirring was continued for 1 hour at the same temperature. The temperature was then gradually raised to room temperature and, at room temperature, stirring was continued for further 3 hours to complete the reaction. The precipitate thus formed was filtered off and the filtrate was concentrated until crystallization occurred. When crystals appeared, the concentration was terminated and the filtrate was cooled until it became 0° C., so as to sufficiently effect crystallization.

The resulting crystals were collected by separation, followed by vacuum drying, to thereby obtain 8294 g (yield: 65.0%) of dibenzyl-bis($\eta$-cyclopentadienyl)titanium crystals. The resulting product was found to have a Ti content of 13.25% (theoretical value: 13.29%), remaining Mg content of 1 ppm and remaining Cl content of 15 ppm. Thus, the quality of the product was fully satisfactory.

Example 4

In a reactor having an internal volume of 200 liters, 110 liters of xylylene as a solvent and 8818 g (30.20 moles) of zirconocene dichloride were charged, followed by sufficient stirring. The internal temperature was then cooled to −10° C. To the resulting suspension, 44.8 liters (1.550 moles/liter, 69.46 moles, 1.15 molar times the theoretical amount relative to the zirconocene dichloride) of a THF solution of p-methoxyphenylmagnesium chloride which had been synthesized by the Grignard reaction was added dropwise at the internal temperature of −8 to −10° C. over 9 hours.

After completion of the dropwise addition, stirring was continued for 1 hour at the same temperature. The temperature was then gradually raised to room temperature and, at room temperature, stirring was continued for further 3 hours to complete the reaction. The precipitate thus formed was filtered off and the filtrate was concentrated until crystallization occurred. When crystals appeared, the concentration was terminated and the filtrate was cooled until it became 0° C., so as to sufficiently effect crystallization.

The resulting crystals were then collected by separation, followed by vacuum drying, to thereby obtain 8948 g (yield: 68.0%) of di(p-methoxyphenyl)-bis($\eta$-cyclopentadienyl) zirconium crystals. The resulting product was found to have a Zr content of 20.90% (theoretical value: 20.94%), remaining Mg content of 1 ppm and remaining Cl content of 15 ppm. Thus, the quality of the product was fully satisfactory.

Example 5

In a reactor having an internal volume of 200 liters, 110 liters of xylylene as a solvent and 10815 g (25.00 moles) of bis(pentamethylcyclopentadienyl)zirconium dichloride were charged, followed by sufficient stirring. The internal temperature was then cooled to −10° C. To the resulting suspension, 34.85 liters (1.650 moles/liter, 57.7 moles, 1.15 molar times the theoretical amount relative to the bis (pentamethylcyclopentadienyl)titanium dichloride) of a THF solution of phenylmagnesium chloride which had been synthesized by the Grignard reaction was added dropwise at the internal temperature of −8 to −10° C. over 6 hours.

After completion of the dropwise addition, stirring was continued for 1 hour at the same temperature. The temperature was then gradually raised to room temperature and, at room temperature, stirring was continued for further 3 hours to complete the reaction. The precipitate thus formed was filtered off and the filtrate was concentrated until crystallization occurred. When crystals appeared, the concentration was terminated and the filtrate was cooled until it became 0° C., so as to sufficiently effect crystallization.

The resulting crystals were then collected by separation, followed by vacuum drying, to thereby obtain 8641 g (yield: 67.0%) of diphenyl-bis(pentamethylcyclopentadienyl) zirconium crystals. The resulting product was found to have a Zr content of 17.65% (theoretical value: 17.68%), remaining Mg content of 3 ppm and remaining Cl content of 15 ppm. Thus, the quality of the product was fully satisfactory.

Example 6

Example 1 was followed, except that diphenylphosphinomethylene magnesium chloride was used as the Grignard reagent. As a result, bis-(diphenylphosphinomethylene)-bis($\eta$-cyclopentadienyl)titanium was obtained as orange crystals. The yield was 62.5%. The quality of the product was fully satisfactory.

Example 7

Synthesis and treatment were carried out in the same manner as in Example 1, except that the reaction solvent was changed to 1,2-dimethoxyethane. As a result, 8294 g (yield: 65.0%) of di-p-tolylbis($\eta$-cyclopentadienyl)titanium was obtained as orange crystals. The resulting product was found to have a Ti content of 13.23% (theoretical value: 13.29%), remaining Mg content of 1 ppm and remaining Cl content of 5 ppm. Thus, the quality of the resulting product was fully satisfactory.

Example 8

Example 1 was followed, except that the Grignard reagent was added dropwise over 2 hours at the internal temperature of 24° C. Since the product thus obtained contained much impurities, recrystallization was repeated for purification. As a result, the di-p-tolylbis($\eta$-cyclopentadienyl)titanium was obtained in a yield of 35%.

Example 9

Example 1 was followed, except that the Grignard reagent was added dropwise over 1.5 hours at the internal temperature of 25° C. Since the product thus obtained contained much impurities, it was difficult to purify the product even by repeating recrystallization. In the end, the yield of the di-p-tolylbis($\eta$-cyclopentadienyl)titanium which was a target compound was 3%.

INDUSTRIAL APPLICABILITY

As described above, a di-substituted metallocene compound having a good quality can be synthesized completely at a low cost in a high yield in a easy manner by reacting a metallocene dihalide with a Grignard reagent which is a compound represented by formula (I) under specified conditions in accordance with the synthesizing process of the present invention.

What is claimed is:

1. A process for synthesizing a di-substituted metallocene compound, which comprises reacting a metallocene dihalide with a compound represented by formula (I): RMgX (wherein R represents an aryl, benzyl or diaryl phosphinomethylene group which may have a substituent, and X represents a halogen element) to produce a di-substituted metallocene compound.

2. The process for synthesizing a metallocene compound according to claim 1, wherein the reaction is effected under conditions which do not cause a side reaction.

3. The process for synthesizing a metallocene compound according to claim 1, wherein the compound of formula (I) is added dropwise to a solution containing the metallocene dihalide at a temperature lower than 25° C. but not lower than −30° C. over 3 to 20 hours.

4. The process for synthesizing a metallocene compound according to claim 3, wherein the compound of formula (I) is added dropwise at a temperature ranging from 15° C. to −25° C. over 5 to 15 hours.

5. The process for synthesizing a metallocene compound according to any one of claims 1 to 4, wherein the compound of formula (1) in a molar amount of 0.9 to 1.5 times the theoretical amount with respect to the metallocene dihalide is reacted with the solution containing the metallocene dihalide.

6. The process for synthesizing a metallocene compound according to any one of claims 1 to 4, wherein the solvent of the solution containing the metallocene dihalide is at least one of a linear ether and a cyclic hydrocarbon.

7. The process for synthesizing a metallocene compound according to any one of claims 1 to 4, wherein the metal atom of the metallocene dihalide is Ti, Zr or Hf.

* * * * *